United States Patent
Soldin (12)

(10) Patent No.: US 6,410,340 B1
(45) Date of Patent: Jun. 25, 2002

(54) USE OF AN 8.4 KDA PROTEIN AS AN IMMUNOPHILIN REAGENT IN PROTEIN BINDING ASSAYS FOR IMMUNOSUPPRESSIVE DRUGS

(75) Inventor: Steven J. Soldin, Bethesda, MD (US)

(73) Assignee: Children's Research Institute, Washington, DC (US)

( * ) Notice: Subject to any disclaimer, the term of this patent is extended or adjusted under 35 U.S.C. 154(b) by 9 days.

(21) Appl. No.: 09/643,723

(22) Filed: Aug. 23, 2000

(51) Int. Cl.[7] .................... G01N 33/567; G01N 33/533; G01N 33/534; G01N 33/535
(52) U.S. Cl. ...................... 436/503; 435/7.93; 436/504; 436/544; 436/545; 436/546; 436/815
(58) Field of Search ................................ 435/7.93, 815, 435/544, 545, 546, 503, 504

(56) References Cited

U.S. PATENT DOCUMENTS 5,525,523 A * 6/1996 Soldin
5,698,448 A * 12/1997 Soldin
6,127,521 A * 10/2000 Berlin et al.

OTHER PUBLICATIONS

Davis & Soldin Biochem. Biophys. Res. Commun. 277:325–329 (2000) "Identification of Ubiquitin as an Immunophilin".

* cited by examiner

Primary Examiner—Mary E. Ceperley
(74) Attorney, Agent, or Firm—Law Offices of Dr. Melvin Blecher; Melvin Blecher

(57) ABSTRACT

We have identified and purified to homogeneity from lymphatic tissues a 8.4 kDa immunophilin that specifically and avidly binds the immunosuppressant drugs FK-506 (Kd=0.8 nM) and rapamycin (Kd=0.08 nM) and their pharmacologically active metabolites and derivatives, but does not bind cyclosporin A. The isolated 8.4 kDa protein appears to be identical to authentic human and bovine ubiquitins in all measured respects (partial amino acid sequence, molecular weight, binding constants, binding specificity, biochemical aspects, and utility as the protein binding reagent in binding assays for immunosuppressant drugs in fluid samples, including patient blood). The availability of commercial quantities of human recombinant ubiguitin removes a supply barrier to the use of immunophilin protein binding assays for the estimation of FK-506, rapamycin and pharmacologically active metabolites and derivatives in the clinical setting.

10 Claims, 6 Drawing Sheets

USE OF AN 8.4 KDA PROTEIN AS AN IMMUNOPHILIN REAGENT IN PROTEIN BINDING ASSAYS FOR IMMUNOSUPPRESSIVE DRUGS

FIELD OF THE INVENTION

The invention relates to protein binding assays for immunosuppressant drugs in body fluids. More specifically, it relates to the isolation of a novel immunophilin from lymphatic tissues that appears to be identical to ubiquitin, and to the uses of both proteins for protein binding assays for FK-506 and rapamycin, and pharmacologically active metabolites and chemical derivatives thereof.

BACKGROUND OF THE INVENTION

FK-506 (also known as tacrolimus), rapamycin (RAP, also known as sirolimus), and cyclosporin A, isolated from soil microorganisms, as well as metabolites and derivatives thereof, are currently widely used in organ transplantation to suppress the immune system, and thereby avoid organ rejection; hence, they are referred to as immunosuppressant agents or drugs.

Such drugs are candidates for precise therapeutic drug monitoring, for several reasons. One, because there are serious consequences of both undermedication (organ rejection) and overmedication (infection and toxic side effects). Two, there are wide intra- and inter-individual variations and narrow therapeutic indices. Three, the immunosuppressant drugs are known to be actively metabolized by the patients, thereby producing a mixture of pharmacologically active and pharmacologically inactive metabolites. Only approximately ⅓, ¾ and ½ of CsA, FK-506 and RAP, respectively, are in the blood in the form of the parent compound; the remainder consists of metabolites of these drugs. It is obvious that analytical methods for use in therapeutic drug monitoring of these immunosuppressant drugs must (a) be able to distinguish pharmacologically active from inactive metabolite species, and (2) do so in a manner proportional to their pharmacological potency.

A wide variety of immunosuppressant drug metabolites have already been identified. Rapamycin (sirolimus) metabolites account for at least 50% of all rapamycin species in trough blood samples, so their potential for interfering in drug assays is quite high. Rapamycin is known to have at least ten metabolites (Yatscoff et al., *Ther Drug Monit* 17:666 (1995)). Metabolites RM1, RM2, RM3 and RM4 have been isolated from the urine of patients receiving rapamycin; only RM1 bound specifically to the 14 kDa immunophilin (21% of parent binding) and to the 52 kDa immunophilin (25% of parent binding) (Davis et al., *Clin. Biochem*. 29: 303 (1996)). Other known rapamycin metabolites include: 7-0-demethyl sirolimus, 41-0-demethyl sirolimus; 32,41-0-demethyl sirolimus, (C9–C23)-OH-sirolimus; and (C1–C8 or C32–C36) OH sirolimus; all but the fourth metabolite substantially binds a 5–8 kDa immunophilin and a 52 kDa immunophilin (Davis et al., *Clin. Biochem*. 33:31 (2000).

Certain chemical derivatives of RAP are also biologically active as immunosuppressants. For example, Rapamycin Derivative (RAD), the derivative SDZ-RAD (40-O-(2-hydroxymethyl)-rapamycin), and the rapamycin metabolite SDZ-RAD 17,18,19,20,21,22-tris-epoxide are all known to be immunosuppressants; [see, e.g., immunosuppressant for lung transplants (Serkova et al., *J. Pharm. Exp. Therap*. 294:323 (2000)), and kidney transplants (Schuurman et al., *Transplantation* 69:737 (2000)].

Tacrolimus (FK-506) metabolites comprise about 30% of the tacrolimus species in blood. Tacrolimus is metabolized into at least nine metabolites (Jusko et al., *Ther Drug Monit*. 17:, 596, 606 (1995)). Structures of several are 13-demethyl tacrolimus, 15-demethyl tacrolimus, and 31-demethyl tacrolimus, and their binding to the 5–8 kDa immunophilin has been studied extensively (Davis et al., *Clin. Biochem.* 33:1 (2000)). The principal metabolites, M-III and M-V, have no pharmacological activity in vitro; the M-II metabolite is pharmacologically active (Soldin, *Clin. Biochem*., 29:439 (1996)). At least one metabolite (31-demethyl tacrolimus) shows immunosuppressive activity equal to that of its parent.

Six methods have been described to date for the analysis of the aforementioned immunosuppressant drugs in patient blood: (1) HPLC; (2) high performance liquid chromatography-mass spectrometry (HPLC-MS); (3) microparticle enzyme immunoassay (MEIA); (4) ELISA; (5) p70-S6 kinase inhibitors; and, (6) an immunophilin-binding assay (IBA). For reviews of the literature comparing these four methods, see, Davis et al., *Clin. Therap*. 22 (Suppl. B): pp B62–70 (2000); Soldin, *Therap Drug Monit* 22:44 (2000). These reviews conclude that HPLC methods suffer from precision problems because of the extensive sample preparation required. HPLC-MS method are not practical for routine clinical use. Initial studies of the MEIA and ELISA have found overestimation of immunosuppressant drug concentrations, possibly because of cross-reactivity of the antibody with drug metabolites that are not pharmacologically active. Monitoring by p70 S6 kinase inhibitions is at present only theoretical, and the assay itself is not yet optimal.

The protein binding reagents preferred for IBAs for FK-506 and RAP and pharmacologically active metabolites are certain lymphatic tissue proteins referred to as immunophilins. It is widely believed that immunophilins may be the intracellular target of the immunosuppressant drugs in a process that leads to suppression of the immune system. Because immunophilins exhibit many of the properties of a physiological receptor, they have been the proteins of choice for use in IBAs. They allow the assay to measure the parent active drug or drug metabolites selectively, even in the presence of structurally similar, but pharmacologically inactive, drug metabolites. The IBA also has the potential to be automated, a valuable characteristic for the clinical laboratory.

Immunophilins of various molecular weights have been purified from the cytosolic phases of lymphatic cells. These include a 10–12 kDa protein (Siekierka et al., U.S. Pat. No. 5,109,112); a 14.6 kDa protein (Soldin, U.S. Pat. No. 5,525,523; 5,354,845); a 17.6 kDa protein (Handschumacher et al. U.S. Pat. No. 4,722,999); a 34–37 kDa protein (Soldin, U.S. Pat. No. 5,780,307); and, a 50–52 kDa protein (Soldin, U.S. Pat. No. 5,698,448).

Although IBAs appear to be the method of choice to monitor blood concentrations of immunosuppressant drugs, commercial use of these IBAs has been thwarted by the lack of adequate supplies of the immunophilins. Supply by actual isolation from lymphatic cells is cumbersome, inefficient and expensive, and may not yield a standard product. Supply by recombinant DNA means would be ideal, but this has not yet been accomplished for the above-mentioned immunophilins. Hence, it would be ideal to have a protein available that exhibits all of the desirable binding assay properties of the known immunophilins and that is commercially available in pure form, preferably as a recombinant protein. This has now been accomplished by the identification, isolation to homogeneity and partial sequencing of a novel 8.4 kDa immunophilin from extracts of lymphatic tissues that appears to be identical to ubiquitin, which is commercially available as a recombinant protein. The discovery of the novel 8.4 kDa immunophilin, the proofs of the identity of this protein to ubiquitin, and the uses of this novel ubiquitin immunophilin in IBAs are described below.

SUMMARY OF THE INVENTION

The inventor has discovered in water-soluble extracts of lymphatic tissues a heretofore unknown protein of 8.4 kDa mass with the binding specificity and binding affinity of an immunophilin specific for FK-506 and RAP, and with no significant binding to CsA.

In a second aspect of the invention, the first 23 amino acids of the 8.4 kDa protein is identical to ubiquitin, a protein heretofore known only as a participant in proteosomal proteolytic degradation of other proteins.

In another aspect of the invention, commercial preparations of ubiquitin, including recombinant human ubiquitin, are shown to exhibit immunosuppressant drug binding specificities and affinities, as well as other biochemical properties, identical to those of the isolated 8.4 kDa immunophilin.

In still another aspect of the invention, commercial ubiquitin, as well as the isolated 8.4 kDa immunophilin, are shown to exhibit high utility as a binding reagent in IBAs.

These and other aspects of the invention will become apparent by reference to the specification and appended claims.

DETAILED DESCRIPTION OF THE PREFERRED EMBODIMENTS

Figure 1:
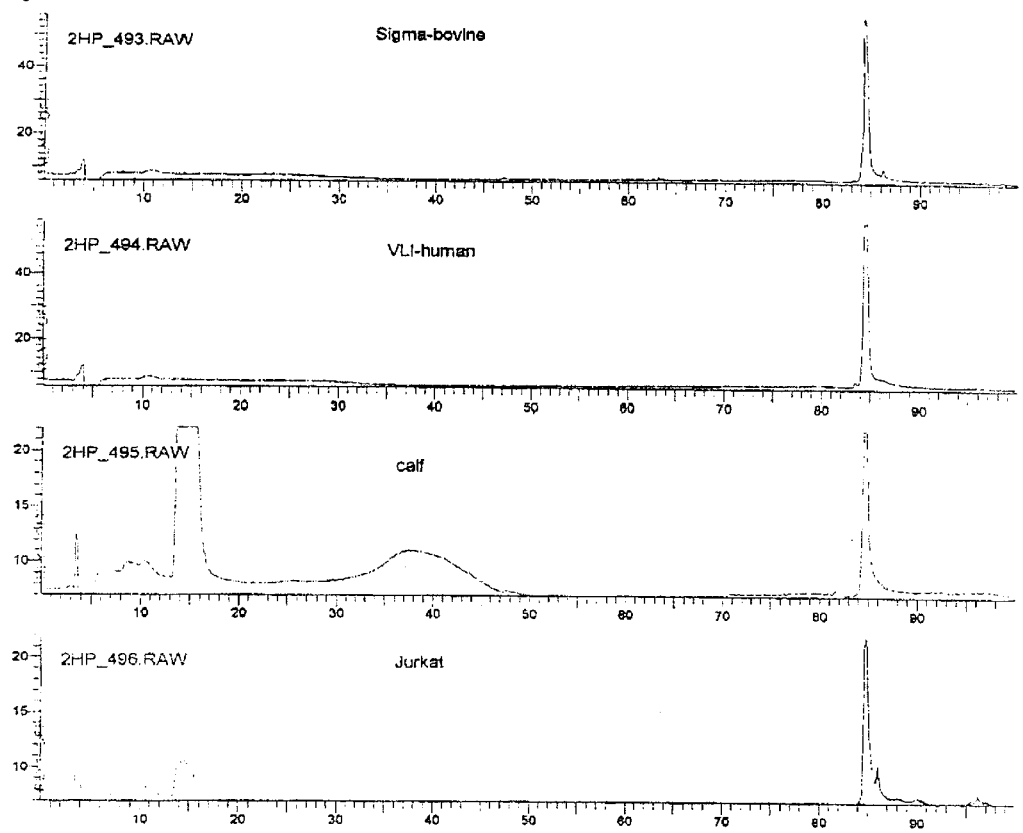
FIG. 1 shows chromatograms from HPLC purification. From top to bottom are: commercial bovine ubiquitin from Sigma-Aldrich; human recombinant ubiquitin from VLI, Inc.; 8.4 kDa protein from calf thymus; and 8.4 kDa protein from Jurkat T cells.

A novel immunophilin of molecular mass 8.4 kDa has been discovered in the soluble cytoplasm of lymphatic tissues. This protein has been isolated and purified to homogeneity, and found to bind avidly the immunosuppressant drugs FK-506 (tarcolimus) and rapamycin (sirolimus), as well as to certain pharmacologically active metabolites and derivatives of these drugs, but not to the structurally dissimilar immunosuppressant drug cyclosporin A.

A startling observation was that the first 23 amino acids of new immunophilin had was identical to that of ubiquitin, a protein heretofore known only as a participant in the mechanisms for degradation of proteins in vivo (for a review, see, e.g., Yamao, *J. Biochem.* 125:223 (1999)). Ubiquitin has not previously been known to interact with immunosuppressant drugs or other immunophilins.

As both recombinant human ubiquitin and bovine ubiquitin are available in commercial quantities, it is now possible to use ubiquitin clinically as the protein binding reagent in IBAs for the drugs FK-506, rapamycin, and their pharmacologically active metabolites and derivatives, in the blood of patients receiving such drugs.

Immunophilins generally can be isolated from cytosolic extracts of target tissues of immunosuppressant drug action by methods previously published (see, e.g., Soldin patents in the Backgound section above and in Davis et al. *Clin. Biochem.* 33:1,31,81 (2000)), namely, mammalian lymphoid tissue or cells such as human peripheral blood lymphocytes, monocytes or leukemia cells, bovine thymus gland, human or calf spleen cells, and human or animal thymoma or lymphoma cell lines. Preferred are lymphocytes, either from solid organs or from tissue culture lines. Most preferred solid organs are spleen and thymus. Most preferred established cell lines are normal or tumor human mononuclear leukocytes. The Jurkat T cell line is highly preferred. It should be emphasized that the particular cell source of the binding proteins of the invention are not important from the perspective of binding assays; the purified protein need only exhibit the desirable binding properties mentioned above and to be described in greater detail below.

A synopsis of methods suitable for the isolation of the inventive 8.4 kDa immunophilin and for it's and ubiquitin's uses in protein binding assays for immunosuppressant drugs will follow.

The soluble cytoplasm or cytosol of a cell is defined in the art as the non-particulate, non-membranous portion of a cell.

The soluble cytoplasm (i.e., cytosol) is defined operationally in this art and herein as that fraction of a cell extract that remains in the supernatant fluid following centrifugation at high g-forces, i.e., greater than 100,000×g, for at least 15 minutes, in an ultracentrifuge such as the the Beckman Model E or successors.

The following art-recognized techniques for disrupting cells and isolating a cytosolic immunophilin are suitable in practicing this invention. Generally, isolated cells are disrupted by one or more methods such as: (1) freeze-thaw cycles at low temperatures in hypotonic solution, followed by gentle homogenization in a glass/glass or Teflon/glass homogenization tube; (2) brief sonication at low temperature in an instrument such as the Brinkman POLYTRON (Brinkman Instruments, Westbury, N.Y.); (3) hypotonic lysis at a low temperature, followed by repetitive forcing of the lysate through a narrow orifice (e.g., a 26 gauge hypodermic needle); or (4) direct homogenization in hypotonic solution. Solid tissues such as spleen or thymus glands can be homogenized at 40° C. using a POLYTRON Tissue Homogenizer and/or a Potter-Elvejhem type Teflon/glass homogenizer in at least 3 volumes of a hypotonic buffer such as a phosphate buffer at pH 7 containing a heavy metal chelator (typically EDTA or EGTA), a disulfide bond protector such a 2-mercaptoethanol, and an inhibitor of proteolysis such as PMSF.

The thus-disrupted cell preparations are fractionated by art-recognized methods to isolate cytosolic proteins. In one technique, the cell homogenate is made up in sucrose (0.25–0.32 M sucrose final concentration), then centrifuged at 100,000×g for 30–90 minutes at 4° C. in vacuo; the immunophilins are in the supernatant fluid, and can be stored frozen (e.g., at −70° C.) until ready for use. In another technique, tissue is disrupted by brief sonication while in an isotonic buffer (e.g., 0.15 M KCl, 20 mM Tris.HCl buffer, pH 7.2, 5 mM 2-mercaptoethanol), the cytosol is recovered by centrifugation at 100,000×g at 40 in vacuo; the immunophilins are in the cytosol, which can be frozen until use. In yet another useful technique, cell debris, after adjusting the mixture to isotonicity, is removed from homogenates by a preliminary centrifugation at 500–1000×g for 10–20 minutes, and the cytosol is obtained by centrifugation of the supernatant fluid at 100,000–150,000×g for 30–90 minutes at 4° C. in vacuo; the immunophilins are in the supernatant fluid. It is clear that, whatever the cell fractionation method, the immunophilin proteins will be located in the water-soluble cytosolic portion of the disrupted cell preparation.

The 8.4 kDa immunophilin of the invention may be purified and concentrated prior to use, as should commercial ubiquitins. Ultrafiltration with CENTRICON MICROCONTRATORS (Amicon, Beverly, Mass.) can be used to preliminarily fractionate immunophilins from cytosols. For example, CENTRIPREP 50 and MACROSEP (Pall Filtron Corp., Northborough, Mass.) produces a fraction containing proteins of molecular masses of <30 kDa. Sequential combinations of conventional size exclusion, HPLC, affinity, ion exchange and hydrophobic interaction chromatographic techniques, and isoelectric focusing using the BioRad ROTOFOR System (BioRad, Hercules, Calif.) and electrophoretic techniques can be used to purify the 8.4 kDa immunophilin to homogeneity. Such fractionation techniques are disclosed in the references cited above. Molecular sieves for fractionating proteins in the 3,000–150,000 molecular weight range include Sephadex G-75 and G-100 (Pharmacia Fine Chemicals, Piscataway, N.J.) and Bio-Gel P-100 (Bio-Rad, Hercules, Calif.). A preferred affinity column is MATREX Gel Blue A (Amicon Corp., Denvers, Mass.) on which immunophilins can be readily fractionated with salt gradients. For HPLC, instruments made by Beckman Instruments Co. and using a Bio-Rad BIOSIL SEC 125 column are preferred. For isoelectric focusing and the determination of pI values, the ROTOFOR instrument of Bio-Rad is preferred. For cation exchange chromatography, a weak cation exchange matrix (Beckman's TSK CM-25W SPHEROGEL) is preferred. Hydrophobic interaction matrices can also be used to fractionate proteins. Purity of isolated proteins can be assessed by SDS-PAGE chromatography.

Any sequence or combination of the aforementioned methods can be used according to this invention as long as proteins of suitable purity are obtained. For the purposes of this invention, a protein is deemed to be "purified" if it produces a single, sharp chromatographic peak on HPLC or single, narrow band on SDS-PAGE.

Analytical data on purified immunophilins may be obtained conventionally. Association constants, specific binding activities, and numbers and types of binding sites can be obtained from Scatchard and Hill plots, using EBDA and LIGAND software. Isoelectric points ("pI") can be obtained by isofocussing techniques. To obtain amino acid composition data, samples can be hydrolyzed by HCl gas in the presence of internal standards (e.g., norvaline and sarcosine), the products derivatized with a fluorescent reagent, and the derivatized amino acids separated on a Hewlett-Packard AMINO QUANT Analyzer. To sequence protein chains, a sample of the protein is reduced and pyridinylated (to protect cysteine residues), freed of reductant and salts, then cleaved by controlled tryptic digestion. Tryptic peptides can be resolved by RP-HPLC and sequenced by standard methods. N-terminus and C-terminus amino acid sequences mar be obtained by art-recognized techniques, including Edman degradation.

The 8.4 kDa immunophilin can also be synthesized by art-recognized recombinant DNA techniques (Olds et al., Principles of Gene Manipulation, 3 d. ed., Blackwell, Boston, 1985, Ch. 1–12; Sambrook et al., Molecular Cloning: A Laboratory Manual, Cold Spring Harbor Laboratory, N.Y., 1989). In brief, immunophilin cDNA may be cloned from purified MRNA or from a cDNA cloning library using oligomers of a sequence deduced from tryptic peptides of at least 7 amino acids in length to produce large amounts of the protein. An expression vector may be constructed containing the immunophilin cDNA, promoter and gene regulation sequences, and then inserted into transformed eukaryotic or prokaryotic expression systems. The immunophilin can be isolated from growth media by the methods according to the invention.

To determine effects of the immunophilin on enzyme activities, the following protocols can be employed. For detection of effects of a immunophilin on a cyclic AMP ("cAMP")dependent protein kinase, mixtures containing enzyme, protein substrate (e.g., a histone or a partially dephosphorylated casein), phosphorylating reagent $\gamma$-$^{32}$P-ATP, activator cAMP, cofactor $Mg^{2+}$, and an immunophilin in a phosphate buffer at pH 6.8 are incubated for an appropriate period, and reaction ended by adding a heavy metal chelator reagent and maintaining the mixture at 100° C. for a brief period (e.g., 2 minutes). Radio-labeled substrate protein may be detected by radioautography of the gel after SDS-PAGE separation of the reactants and products. Autoradiograms may be quantified by a densitometer using transmittance scanning at 600 nm. Immunosuppressant drugs (e.g. 60–600 nM) may be added to incubation mixtures to determine their effect, if any, on the immunophilin effect.

Autophosphorylation of lck tyrosine-specific protein kinase, which is activated by the CD 4/CD 8 receptor early in T-cell activation, in the presence of immunophilins may be tested according to the procedure of Veillette et al., *J. Exp. Med.*, 170:1671 (1989); Veillette et al., *Nature*, 338:257 (1988).

Protein kinase C activity may be analyzed using the rat brain enzyme and a procedure developed by Amersham Corp. Briefly, the enzyme catalyzes the transfer of the $\gamma$-phosphate from $\gamma$-$^{32}$P-ATP to a threonine-containing peptide substrate in the presence of an enzyme activator such as phorbol 12-myristate 13-acetate, cofactors $Mg^{2+}$ and $Ca^{2+}$, and a mixed micellular suspension containing L-$\alpha$-phosphatidyl-L-serine and the phorbol. Phosphorylated peptide is separated on binding paper, washed with dilute weak acid, and the phosphorylation of the peptide substrate detected and quantified by scintillation counting. To test for effects of immunophilins on this reaction, the immunophilin±immunosuppressive drug is present during the incubation.

Rotamase activity (cis-trans peptidyl-prolyl isomerase activity) may be assayed in purified inmunophilins using the methods of Fischer et al., *Nature*, 337:476 (1989) and Lange et al., *Nature* 4 331:453 (1988), which are incorporated herein by reference.

For the purpose of an IBA according to this invention, the 8.4 kDa immunophilin or ubiquitin are deemed acceptable if: (1) the protein binds immunosuppressant drugs (FK-506, rapamycin, pharmacologically active metabolites and derivatives thereof) to a statistically significant extent (as this expression is understood in the ligand binding protein art), based upon the method of detection, i.e., radioactivity, fluorescence polarization, chemiluminescence and the like; (2) unlabeled drug and pharmacologically actives and metabolites thereof reversibly compete with labeled drug for specific binding sites on the protein; and (3) the signal-to-noise ratio, i.e., the ratio of total binding of labeled drug to nonspecific binding of this molecule (as these terms are defined in *Principles of Competitive Protein Binding Assays* infra) is at least 1.1, preferably at least 1.2.

Labeled Drugs

For the protein binding assays using the immunophilins of the invention of the invention, labeled immunosuppressive drugs are required. Where the label is radioactivity, FK-506, rapamycin and CsA labeled with $^3$H or $^{125}$I are available commercially from Amersham Corp. (Chicago, Ill.). [$^3$H] CsA (label positions: 95% [Abu-$^3$H]-cyclosporine and 5% ([N-methyl-$^3$H]-Sar) cyclosporine is available from Sandoz Pharmaceuticals, Hanover, N.J. or Sandoz Ltd. Basel, Switzerland (SANDIMMUNE®). [$^{125}$I]-CsA is sold by Immuno Nuclear Corp., Stillwater, Minn., 55082 as part of their INCSTAR kit as CYCLOTRAC®. MeBut-β-[$^3$H]-CsA, specific activity 5–20 Ci/mmol, is available from the Amersham Corp., Arlington Heights, Ill.

For fluorescent polarization detection methods, CsA-fluorescein tracer, suitable for use with the TDX instrument, is available from Abbott Laboratories, Abbott Park, Ill. FK-506, RAP, CsA and pharmacologically active metabolites and derivatives thereof can also be labeled with fluorescein by reaction with fluorescein isothiocyanate according to Mahoney, W. C., et al., U.S. Pat. No. 4,427,035. *Chem.*, 32:492 (1986)]. CsA, CsB, CsC and CsD and CsA metabolites for use as standards are available from Sandoz Pharmaceuticals, Hanover, N.J. [$^3$H]-Dihydro FK-506 can be prepared by exposure of native FK-506 (Fujisawa Pharm. Co., Osaka, Japan) to $^3$H$_2$ in the presence of a reducing agent (e.g., Tris-(triphenyl phosphine) rhodium I chloride), followed by purification by normal and reverse phase chromatography (Amersham Corp.). Purification can be assessed by TLC. One preparation of [$^3$H]-dihydro FK-506 was 98+% pure by three different TLC systems, and had a specific activity of 51 Ci/mmol (63.2 mCi/mg). $^{125}$I-FK-506 can be prepared by brief reduction by chloramine-T in the presence of Na$^{125}$I. $^{125}$I-labeled histamine-FK-506 can be produced according to Wong et al. 1986 above. FK-506 may be labeled with a fluorophore by art-recognized methods (Mahoney, W. C. et al., above).

Rapamycin (Wyeth-Ayerst Pharm. Co., Princeton, N.J.) and pharmacologically active metabolites and derivatives thereof can be labeled with $^3$H by art-recognized methods such as exposure of native rapamycin to tritium gas in the presence of a reducing agent, followed by purification by normal and/or reverse phase chromatography. Purification can be assessed by TLC. One preparation of [$^3$H]-rapamycin, which was 98+% pure as determined by TLC, had a specific activity of 13.6 Ci/mmol.

Chemiluminescent labels such as water soluble 1,2-dioxetanes that are activated by cleavage by alkaline phosphatase or α- or β-galactosidases have been described by Bronstein et al.,*J. Biolumin. Chemilumin.* 2:186 (1988)] and Voyta et al. *Clin. Chem.* 34:157 (1988)], and can be purchased from Tropix, Inc. Bedford, Mass. 01730 (cat. no. ED-010).

Standard and metabolite preparations are produced according to published methods (see, e.g., Davis et al., *Clin. Biochem.* 33:1 (2000)). Pharmacologically active metabolites of FK-506 include 31O-methyl FK-506. The counterparts for RAP include 7-O-demethyl RAP, 41-O-demethyl RAP, 32,41O-demethyl RAP, (C9–C23)-OH RAP, and (C1–C8 or C32–C36)-OH-RAP. RAP derivatives are listed above.

Protein Binding Assays Using An Immunophilin

An immunophilin protein binding assay ("IBA") carried out in accordance with this invention can be performed by solution phase or solid phase methods. The basic principle underlying each method is the same, and is described in, e.g., Davis et al., *Clin. Biochem.* 33:1(2000) and the Soldin patents listed above. Briefly, in a competitive IBA, a competition equilibrium is set up between a tracer amount of labeled drug and the corresponding drug in unknown samples containing the drug or biologically-active metabolites for binding to specific binding sites on an immunophilin. Following attainment of equilibrium, the amount of labeled drug bound to the immunophilin is determined. The amount of labeled drug bound will be reduced in proportion to the amount of analyte in a biological sample being analyzed. The quantitative relationship between the reduction of immunophilin-bound labeled drug and the concentration of the analyte in the unknown sample is determined by reference to a standard calibration curve. To generate such a curve, a fixed amount of binding protein is contacted with a fixed tracer amount of the labeled drug in the presence of zero-to-supersaturating concentrations of standard drug. It is preferred that this supersaturating concentration be several orders of magnitude greater than the association constant, $K_a$, of specific binding, and this fraction, which is termed "nonspecific binding" ("SB"), is assumed to be the same for all ligand concentrations, as NSB is assumed to be a linear function of ligand concentration. The amount of NSB binding is subtracted from each data point in order to obtain "specific binding". The amount of labeled drug bound to an immunophilin need not be determined directly; it may be determined by subtracting from the total amount of label added remaining unbound in the solution at equilibrium.

Solutions of Immunosuppressive Drugs

Standard solutions of immunosuppressive drugs for use in the assays according to the invention are prepared as follows. Stock solutions of drugs (typically containing 10–20 μg/mL, but other concentrations may be appropriate) may be prepared in a polar solvent miscible with water (e.g., 50% ethanol). For use in producing a calibration curve, aliquots of this stock standard solution may be delivered to assay tubes and the solvent removed (stream of N$_2$ or in vacuo), or the stock solution may be appropriately diluted in drug-free whole blood, plasma or serum, to produce a working standard. Further dilutions in drug-free whole blood, plasma or serum are made to produce a series of diluted standard solutions with immunosuppressive drug concentrations ranging from 0 to 2000 ng/mL. The concentrations of solvent remaining in the working standard solutions are not critical as long as they are without influence on the binding reactions. Standard working solutions of drugs at the highest level can be stored at 4° C., but should be used within 24 hours of its preparation. Alcohol is a preferred solvent and is selected from among $C_1$ to $C_8$ primary, secondary or tertiary alkanols. Acetonitrile is also suitable as a solvent for stock solutions of cyclosporines. Most preferred in 50–70% aqueous ethanol.

Extraction of Drugs from Fluid Samples Prior to Assay

Immunosuppressant drugs and their metabolites and derivatives (collectively, "analytes") in patient samples such as whole blood, serum or plasma must be placed in a form suitable for assay, in particular to separate the drug from interfering chemicals such as other therapeutic drugs.

Separation of analytes from interfering chemicals can be accomplished by extraction procedures. For example, analyte-containing fluid samples are extracted with about 20 volumes of an amphipathic solvent, and the precipitated proteins sedimented by centrifugation. By "amphipathic organic solvent" is meant a liquid organic compound having both hydrophilic and hydrophobic moieties. Preferred amphipathic alcohols are lower alkanols (e.g., $C_1$–$C_6$ straight or branched chain, primary, secondary or tertiary alcohol) or acetonitrile. It is also suitable to extract an aliquot of whole blood with an amphipathic surfactant solution. For example, 5–10 volumes of 20 mm Tris buffer, pH 8.5, containing 0.03% (v/v) Tween 20 polyoxyethylene (20 sorbitan monolaurate) is a suitable extractant (Felder, R. A., supra). Drugs and their metabolites can also be extracted from serum-containing samples by the method of Yee et al., *Clin. Chem.*, 28:2269 (1982), using a Baker 10 extraction system (SPE, J. T. Baker, Phillipsburg, N.J.) and small cyano disposable extraction columns (3 mL. capacity, 40 mm diam.). In another technique suitable for whole blood, which may also contain other drugs that may produce spurious results, a sample of whole blood is extracted with an amphipathic solvent, e.g., 2 volumes of methanol and one volume of water, the precipitated proteins are removed by centrifugation, and the supernatant fluid containing the drug either filtered through Sep-Pak $C_{18}$ sample preparation cartridges (Waters Chromatography Division, Milford, Mass.) according to the method of Charles et al., *Therap. Drug Monitor*, 10:97 (1988), or through a reversed phase hydrophobic adsorbent matrix such as the BOND ELUT® sorbent minicolumns (Varian Assoc., Harbor City, Calif.). The latter column of the cyclohexyl type separates FK-506 from CsA, as well as from immunosuppressive drugs such as prednisolone. The BOND ELUT® column, in conjunction with the above-described extraction step, produces background levels of <1 μg/L, the minimum detectable concentration in the assay methods according to the invention. Void volumes from these columns are taken to dryness, and analyte drugs assayed as described above and below.

Solution Phase Assay Procedure

1. Binding Step

Aliquots of extracts containing unknown analyte or standards or labeled analyte (the sizes of these aliquots are dependent upon the label, but typically range from 0 μL to about 1000 μL when using $^3$H- or $^{125}$I-labeling), are added to reaction tubes and the solvent removed at a slightly elevated temperature using a gentle stream of an inert gas, typically 40° C. and $N_2$ gas, or in vacuo. To each reaction tube is added a fixed tracer amount (e.g., 0.5 nM, 50–100,000 CPM) of labeled drug in a small volume (typically 50 μL) of solvent.

Thereafter, an aliquot of an appropriate dilution of the immunophilin preparation in binding buffer (e.g., 100–200 μL) is added to the reaction tubes, and the mixture is incubated with shaking to allow the analyte preparation to reach equilibrium binding with the protein. An aliquot of labeled drug is added to the test tube and mixed. The tubes are then incubated for a period suitable for reaching equilibrium binding, ranging from 0 hour (control) to 16 hours, preferably 30–90 minutes, at a slightly elevated temperature, typically, 30–40° C. Nonspecific binding tubes are also prepared by adding immunosuppressive drug-free extract to the volume of buffer equal to the volume of the binding protein aliquot, and adding a supersaturating concentration (e.g., 200-fold molar excess) of standard drug in a small volume (e.g., 50 μL). The composition of the binding reaction buffer is not critical. A preferred binding buffer is 20 mM Tris buffer, pH 7.2, containing 5 mM μ-mercaptoethanol, 0.05% $NaN_3$ as preservative, and about 7.5% (w/v) fetal calf serum to reduce nonspecific binding.

2. Separation Step

When using any detection methods other than fluorescence polarization methods (which can distinguish protein-bound fluorescein-labeled drug from unbound fluorescein-labeled drug when both are together in solution, see infra), it is necessary to separate the protein-bound labeled drug from free labeled drug.

Among the separation methods useable for this purpose are:

Method A: The contents of the binding reaction mixture are diluted with ice-cold buffer, preferably about pH 7.4, the contents filtered through a glass fiber filter such as Whatman GF/B filters (Whatman Paper, Maidstone, England), then washed with ice-cold buffers; the membrane retains the protein-bound labeled drug.

Method B: This method is the same as Method A, except that filtration is carried out using a microporous filter, e.g., a nitrocellulose 0.22 μm filter (Millipore Corp., Bedford, Mass.) prewashed with a solution of carrier bovine serum albumin or γ-globulin to block nonspecific binding sites; protein-bound drug is retained by the membrane.

Method C: Following dilution of the binding reaction mixture with ice-cold buffer, a suspension of charcoal particles coated with a carrier protein (albumin or γ-globulin) to block nonspecific binding is added to the tube, the mixture vortexed, then centrifuged in the cold to sediment the charcoal particles. The supernatant fluid contains the protein-bound labeled drug.

Method D: Following dilution of the binding reaction mixture with ice-cold buffer, a suspension of polyethylene glycol particles (M.W. 15,000–20,000), e.g., 1.0 mL of a 30 mg/mL suspension, plus a solution of a carrier protein, preferably about 1.0 mg of serum albumin or γ-globulin, are added, and the resulting suspension is mixed. The sediment is collected by centrifugation and the supernatant fluid discarded. The pellet contains the protein-bound labeled drug.

Method E: Following dilution of the binding mixture with ice-cold buffer, carrier albumin or γ-globulin is added to the tube, and trichloroacetic acid added to a final concentration of about 5–10% at 0–4° C. to precipitate all proteins. The precipitate is centrifuged and the supernatant fluid discarded. The pellet contains the protein-bound labeled drug.

Method F: Protein-bound labeled drug is separated from the unbound species in the binding mixture using minicolumns of a molecular sieve matrix, such as LH-20 Sephadex (Pharmacia Fine Chemicals, Piscataway, N.J.). Washing the column with a small volume (e.g., 0.5 mL) of phosphate-buffered saline, preferably about pH 7.4, will elute, in the void volume the protein-bound labeled drug. Sephadex LH-20 is a weakly hydrophobic matrix, and free labeled CsA, FK-506 or rapamycin will be retarded in such a matrix.

When $^3$H is the tracer in Methods A and B, the filters are placed in liquid scintillation counting (LSC) vials, and an aliquot of an aqueous-organic solvent phase combining scintillation system (e.g., PCSS, Amersham) is added. The vials are vortexed, and the amount of radioactivity quantified by liquid scintillation spectrometry (LSS). When using Method C, an aliquot of the supernatant fluid is added to LSC vials, diluted with, e.g. PCSS, vortexed, then counted by LSS. When using Methods D and E, the pellet is resuspended in PCSS, or dissolved in NaOH and diluted in PCSS, added to LSC vials, then counted by LSS. When using Method F, an aliquot of the void volume is diluted in PCSS and added to LSC vials, then counted by LSS.

When $^{125}$I is the tracer, the filters from Methods A and B, the supernatant fluid in Method C, the pellets from Methods D and E, or the void volume from Method F, are placed in a tube, and the radioactivity is quantified in a gamma counter.

When chemiluminescent labels are employed, in separation Methods A and B supra, the filters are placed on a sheet of Whatman blotting paper. The filter is then soaked with a solution (500–1,000 µg) of 3-(2'-spiroadamantane)-4-methoxy-4-(3"-phosphoryloxy)phenyl-1,2-dioxetane disodium salt (AMPPD, Tropix, Inc., Bedford, Mass.) in an alkaline buffer containing $MgCl_2$. The filters are transferred to a piece of Mylar polyester film, and then to a black box containing instant film, such as Type 612 Polaroid film. After exposure of the film to the light for an appropriate period, the dark image is digitized using, for example, a black and white RBP Densitometer, Tobias Assoc., Inc., Ivyland, Pa.

In separation Method E, the pelleted suspensions are washed with pH 7.4 buffer, and once with an alkaline buffer (pH 7–10) containing $MgCl_2$. The pellets are then reacted with AMPPD in an alkaline buffer (pH 7–10) containing $MgCl_2$ until maximum luminescence is attained, typically in 15 to 30 minutes at 30° C. Thereafter, the luminescence from each tube is read in a luminometer, e.g., Turner 20E LUMI-NOMETER or Berthold CLINILUMAT Luminescence Analyzer.

In separation Methods C and F, the supernatant fluid or the void volume respectively, are reacted with AMPPD at an alkaline pH (pH 7–10) in the presence of $MgCl_2$. After maximum chemiluminescence has been attained, typically in 15 to 30 minutes at 30° C., the luminescence is estimated in a luminometer.

Where the drug is conjugated to an α- or β-galactosidase, 3(2'-spiroadamantane)-4-(3"-O-galactopyranoside)phenyl-1,2-dioxetane will be the substrate.

The principle underlying fluorescence polarization-based assays is described by Robbins et al., *J. Clin. Lab. Anal.*, 2:62 (1988) and in Abbott Laboratories 55TDX Instruction Manual. In brief, in this assay, a beam of plane polarized light is used to excite the fluorophore (e.g., fluorescein), and the resulting polarized fluorescent signal is measured. The assay depends on the principle that molecules in solution randomly move and rotate at a rate that is inversely proportional to their size. Small molecules (e.g., drug fluorescein) rotate freely and rapidly, whereas large molecules (e.g., protein-bound CsA-fluorescein) will not rotate freely, or as freely.

In the fluorescence polarization binding protein-based assay carried out in accordance with this invention, fluorescein-labeled CsA, FK-506 or rapamycin will not produce polarized fluorescent signal as these molecules rotate freely, whereas the same molecules bound by the cyclosporine binding protein will give a polarized fluorescent signal as they are not free to rotate. That is, polarization increases as molecular size increases.

The assay system thus involves a standard competitive protein binding assay with incubation of a sample containing immunosuppressive drug analyte, fluorescent-labeled drug (e.g., FK-506-fluorescein), and a purified immunophilin. The intensity of the polarized fluorescent signal is inversely related to analyte concentration. Dadliker et al., *Methods Enzymol.* 48:380 (1978). Therefore, if a sample contains a low concentration of drug analyte, after the competitive binding reaction reaches equilibrium there will be a high concentration of bound tracer (e.g., FK-506-fluorescein) in the reaction mixture, and polarization will be high. Conversely, if there is a high concentration of drug analyte in the patient sample, after the competitive binding reaction attains equilibrium, there will be a low concentration of bound tracer in the reaction mixture and polarization will be low. This method is most useful for measurement of small molecules, which produce the greatest change in polarized fluorescence when the labeled molecule is bound to a receptor.

For the purposes of competitive IBA carried out in accordance with this invention, it is an important feature of the fluorescence polarization technique that protein-bound and unbound cyclosporine analyte can be distinguished in a single reaction mixture, i.e., without the need to separate the two components.

Abbott Laboratories has adapted the fluorescence polarization system to assays of multiple therapeutic drugs in its TDX System. The TDX system for the immunoassay of cyclosporine contains, in addition to the automated TDX instrument, a metabolite reagent pack containing, in separate vials, a buffer-surfactant solution, a solution of anti-CsA antibody containing a protein stabilizer, and CsA-fluorescein in a solution containing a surfactant and protein stabilizer. This TDX system is adaptable for a competitive protein binding assay carried out in accordance with this invention for immunosuppressive drugs by replacing the antibody vial with one containing a purified immunophilin according to the invention, and a protein stabilizer.

Drug standards, controls, and patient samples are placed in individual cartridges of the Abbott TDX instrument. The metabolite reagent pack is placed in the instrument. Thereafter, in an automated series of steps, standards, controls and patient samples are mixed with water-soluble binding protein and fluorescein-labeled drug, the mixtures are incubated at the preset temperature for a selected period until binding steady state is reached. The mixtures are transferred to glass cuvettes, and the fluorescent polarization signal measured. As noted above, the intensity of this signal is inversely related to the concentration of the analytes.

The fluorescent signals from patient samples are converted to $B/B_0$ ratios and these ratios are read off of a standard curve obtained by analyzing by fluorescence polarization a series of drug standards (see supra), wherein the ordinates for the standard curve are:

$$[B_{(std)}/B_{(0\ std)}]100\ \text{vs.}\ \log[\text{Drug}]$$

and $B_{(std)}$ is the fluorescence polarization of a bound standard CsA-fluorescein complex, $B_{(0\ std)}$ is that of a control sample and [Drug] is the concentration of immunosuppressive drug at each point.

Assay for Immunosuppressant Drugs in Blood

In a preferred assay, the drug is extracted from blood by the BOND ELUTE (C18) column procedure described above. To the solvent-free dried residue containing the drug is added 50 µL $^3$H-drug (300,000 DPM in ethanol), 100 µL of binding protein solution and 100 µL of buffered 0.2% Tween-20. The mixture is mixed briefly (e.g., 10 secs.), then incubated with shaking for 20 mins. at 25° C. The procedure results in a quantitative recovery of CsA from the dried residue. A portion (200 µL) of this solution is added to a LH-20 Sephadex column (1.8 µL bed volume) equilibrated with 20 mM Tris buffer pH 7.2 containing 5 mM 2-mercaptoethanol and 0.05% sodium azide. Elution of the column with 1.25 mL of column buffer in 250 µL portions completely separates free from bound drug; bound ligand appears in the eluate. The bound radioactivity in the 1.25 mL column eluate is measured in 10 mL OPTIMA GOLD Scintillation Cocktail (Packard Chemicals, Meriden, Conn.) by liquid scintillation spectrometry. Non-specific binding is estimated using a 1 mg/mL concentration of unlabeled drug; at this concentration, the unlabeled drug displaces at least 95% of bound labeled ligand from drug binding sites and thus binding is used to define non-specific binding.

Solid Phase Assays

To immobilize an immunophilin, a supporting matrix, e.g., the bottoms of wells of a microtitre plate, the walls of a plastic tube or polymeric beads, is coated with an immunophilin binding protein and nonspecific binding sites are blocked by brief exposure to a protein such as serum albumin or drug-free serum. A solution of labeled drug is contacted with the coated surface, incubated with gentle shaking, the solid surface washed with cold buffer (e.g., PBS), and the wash fluids aspirated to waste. Thereafter, in a displacement-type reaction an aliquot of fluid sample extract containing analyte drug is contacted with the immobilized immunophilin, and incubated with gentle shaking for a suitable period ranging from 0 hours (control) to 16 hours (analyte). The incubation fluid is aspirated to waste, and the solid surface is washed gently with cold buffer. Protein-bound labeled drug is extracted from the solid surface by surfactant or an amphipathic organic solvent, as described above for extraction of analyte drugs from fluid samples. The precipitated proteins are removed by brief centrifugation, and the amount of label in the supernatant fluid quantified as described above.

Although methods of use of the immunophilins according to the invention are described above in terms of a competitive or sequential IBA involving only a single protein species, it is within the scope of the invention to use such binding proteins in other types of binding assays for immunosuppressant drugs. For example, immunophilins of the invention can be used in simple or cassette-type "double receptor" specific binding assays. "Receptor" in this context refers to any specific binding protein and, in this context alone, also includes antibodies.

Double receptor binding assays have as their salient feature a first receptor specific for a second receptor, the second receptor ordinarily also capable of binding a ligand, generally the analyte (see, e.g., Litt, U.S. Pat. No. 4,092,408, which is incorporated herein by reference). In the present invention, the first receptor, which is advantageously immobilized, is a specific antibody directed to the purified immunophilin, the second receptor is the purified immunophilin itself, and the analyte ligand is an immunosuppressive drug. The binding assay with this system can be either of the direct competitive or sequential displacement types described above. In the latter type, in a first step the second receptor binds labeled drug and in a second step unlabeled drug displaces a portion of the protein-bound label, the degree of displacement being proportional to the amount of analyte present.

Alternate to the double receptor binding assays described above is a modification wherein the immunophilin second receptor is covalently bound to a small organic compound hapten, and the first receptor is an antibody directed against the hapten (see, e.g., Bunting, U.S. Pat. No. 4,271,140, which is incorporated herein by reference). In this system, the second receptor is an immunophilin and the hapten is an organic compound of a molecular weight of less than about 1,000; preferred are haptens such a fluorescein, acridine, dinitrobenzene, or naphthylamine. No more than 20, ordinarily 1 to 5, haptens per mole will be conjugated to an immunophilin.

Double receptor binding assays of either type improve accessibility of the analyte ligand to binding sites on the second receptor. The advantage of the modified double receptor binding assay is that binding affinities between the antibody and the hapten attached to an immunophilin will generally be greater than that between the two proteins without conjugated hapten. This advantage permits the use of insoluble double receptors in automated rechargeable binding assay systems.

For the convenience of the practitioner of the invention, it is within the scope of this invention to provide mercantile kits containing, in separate containers, in solution or immobilized on a solid support, one or more of the purified immunophilins proteins, standards, and labeled immunosuppressant drugs.

Isolation of Immunosuppressant Drugs from Extracts

The high affinities of the proteins of the invention for immunosuppressive drugs and their biologically-active metabolites, and the cross-reactivities of certain members of the class for compounds as similar in structure as the macrolides FK-506 and rapamycin or as dissimilar to the former as the cyclicundecapeptide cyclosporines, indicates that the proteins of the invention may be useful as affinity adsorbents for screening candidate compounds for potential therapeutic or diagnostic usefulness. For example, it is an embodiment of the invention to use the purified proteins of the invention as affinity adsorbents in the methods for screening extracts of fermentation broths of microorganism strains similar to those that produce cyclosporines, FK-506 and rapamycin for the presence of novel compounds of related structures. For rapid screens, the extract or broth is contacted with one or more binding proteins, preferably immobilized on a solid support, to form a protein-compound complex, the complex is washed to remove contaminating substances, the complex is dissociated, and the compound of interest isolated. Solid supports for such immobilization include polymeric (e.g., latex) beads or plastic surfaces. In another embodiment, such affinity adsorbents may be used for preparative-scale isolation of compounds identified by the aforementioned preliminary screen. For such purposes, the immobilized affinity adsorbent may be used in preparative column chromatography, in a batch mode, or in a continuous mode in which the adsorbent is first coated on the inner surface of plastic tubing as a reactor. Alternate to the use of binding proteins themselves as affinity adsorbents, binding proteins may be used to raise polyclonal and/or monoclonal antibodies (the latter increasing specificity), and the antibodies used as immunoaffinity adsorbents in the same manner as described above.

As mentioned above, identification and isolation from body fluids of metabolites of immunosuppressant drugs, particularly biologically active metabolites, is important for studies assessing the contributions of such metabolites to assay values. The purified binding proteins of the invention, particularly in immobilized form, can be used to capture metabolites of FK506 and rapamycin from body fluids in a manner similar to that described above for fermentation broths.

FK506 and rapamycin are produced by microorganisms. No counterpart mammalian compounds are yet known. In order to isolate and identify natural, mammalian immunosuppressant "drugs," the purified binding proteins of. the invention, particularly in immobilized form, can be used to capture material ligands from mammalian body fluids and tissues by methods similar to those described above for the capture of drugs from fermentation broths and drug metabolites from body fluids.

Those skilled in the art of affinity adsorption will undoubtedly conceived of additional uses of the proteins of the invention that fall within the scope of this invention.

In order that those skilled in the art can more-fully understand this invention, the following examples are set forth. These examples are given solely for illustrative purposes, and should not be considered as expressing limitations unless so set forth in the appended claims.

EXAMPLES

Example 1
Isolation and Characterization of the Novel 8.4 kDa Immunophilin

Using protein purification techniques previously published (see, e.g., Davis et al., *Clin. Biochem.* 33:1, 31, 81 (2000)) and cited and described above, an 8.4 kDa immunophilin was isolated and purified to homogeneity from calf thymus and Jurkat T-cells.

Matrix assisted laser desorption ionization mass spectrometry (MALDI-MS) was performed by the HHMI Biopolymer/W. M. Keck Foundation Biotechnology Resource Laboratory at Yale University, New Haven, Conn. on both proteins after C-18 ZIPTIP (Millipore, Bedford, Mass.) to remove interfering substances. Major species were detected at molecular weights of 8440.5 and 8442.4, respectively. The expected deviation of this technique in a linear mode is +/−0.25%, suggesting that these two proteins have identical molecular weights.

The protein isolated from Jurkat cells was further purified using,an HPLC system described elsewhere (Williams et al., *Mol. Biotechnol.* 8:155 (1997). A major sharp peak was observed and collected. The protein in this eluate exhibited excellent binding to FK-506 and RAP. MALDI-MS revealed a mass consistent with those described above.

Example 2
Sequencing of the 8.4 kDa Immunophilin Amino Acid

The sequence determined for the first 23 amino acids was: MET GLN ILE PHE VAL LYS THR LEU THR GLY Seq. ID No. 1 LYS THR ILE THR LEU GLU VAL GLU PRO SER ASP THR ILE.

A search by the National Center for Biotechnology Information at the National Institutes of Health, Bethesda, Md. showed that this sequence was a 100% match for the ubiquitin protein found in a wide range of species, including humans and bovines. The calculated mass for the first 74 amino acid residues of human ubiquitin was 8446.6, which is in excellent agreement with the masses observed for the 8.4 kDa immunophilin (see Example 3), as well as with the mass of 8451 originally described (Schlessinger et al., *Biochem.* 14:2214 (1975)). It should be noted that it is now known that there are actually 76 amino acid residues in human ubiquitin; however, two of these (the glycine-glycine dipeptide at the C-terminal end of the molecule that participate in the mechanism by which ubiquitin covalently binds to other proteins [Hochstrasser, *Science* 289:563 (2000]) are labile and lost during use in protein degradation steps. Therefore, a ubiquitin protein with a mass consistent with 74 amino acid residues is to be expected.

Example 3
Comparisons of the 8.4 kDa Immunophilin and Authentic Ubiquitin

Recombinant human ubiquitin (VLI Research, Malvern, Pa.) and bovine ubiquitin (Sigma-Aldrich, St. Louis, Mo.) were further purified by HPLC (Keck Foundation) in tandem with the isolated calf thymus and Jurkat T cell 8.4 kDa immunophilins. FIG. 1 shows that the retention times on HPLC of the 4 proteins were virtually identical.

The eluates of each of the peaks shown in FIG. 1 were tested for binding to tritiated FK-506 as described above; all four eluates bound the drug with specificity and high affinity.

MALDI-MS was performed on the preparations of the two commercial ubiquitins. The recombinant human and bovine ubiquitins had masses of 8474 and 8475, respectively, which is consistent with a 74 amino acid residue ubiquitin.

Figure 2:
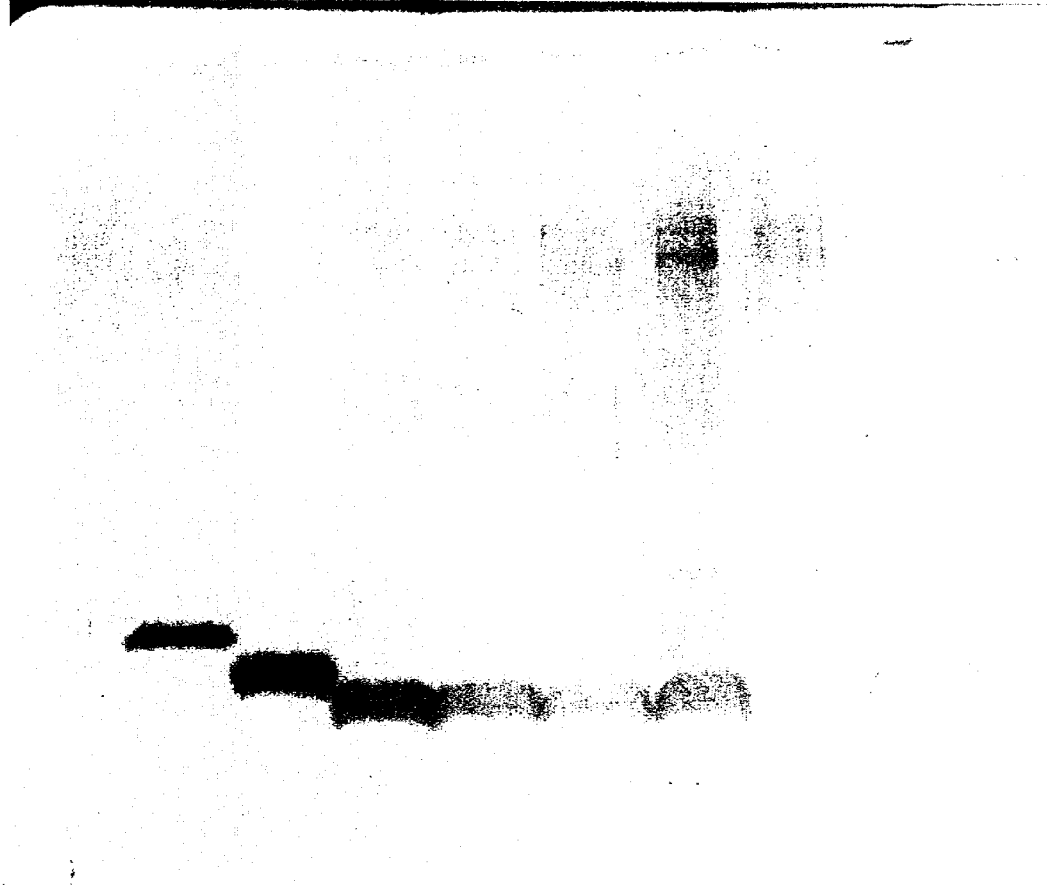
FIG. 2 shows SDS-polyacrylamide gel electrophoresis of 8.4 kDa proteins arising from an isoelectric focusing preparation at pH6.0–7.5.

FIG. 2 shows the SDS-PAGE patterns of the 8.4 kDa immunophilins isolated from calf thymus and Jurkat T cells. The proteins came from isoelectric focusing at pH 6.0–7.5. The proteins from left to right are: 14 kDa marker; 6.5 kDa marker; calf thymus 8.4 kDa immunophilin; Jurkat T cell 8.4 kDa immunophilin, >30 kDa calf thymus cytosol; buffer and loading gel blank; and a 8.4 kDa preparation used for metabolite studies. Although ubiquitin has a molecular weight of 8.4 kDa, it migrates on SDS_PAGE as a 5.5 kDa band, perhaps because of incomplete folding (Haas et al., *Prep. Biochem.* 15:49 (1985)). The migrations on the gel are consistent with the isolated 8.4 kDa immunophilins being ubiquitins.

Figure 3:
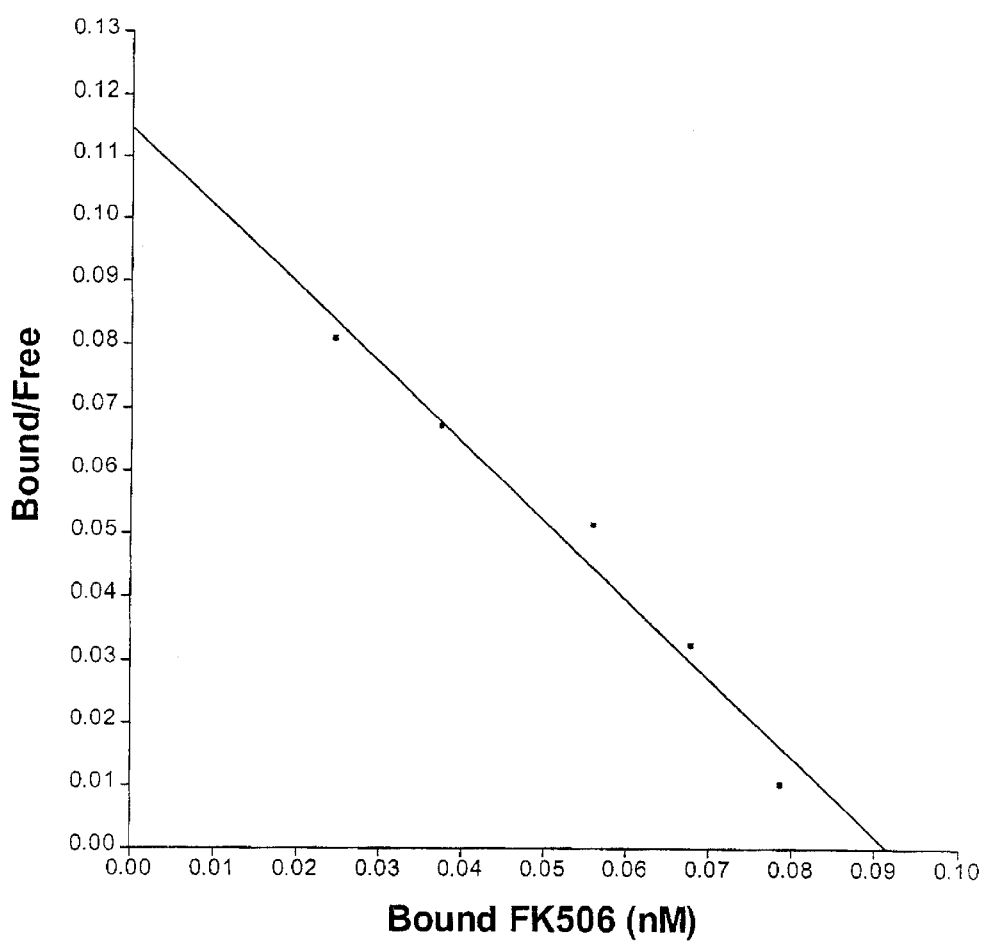
FIG. 3 shows a Scatchard plot for the binding of radioactive FK-506 to 8.4 kDa immunophilin.
Figure 4:
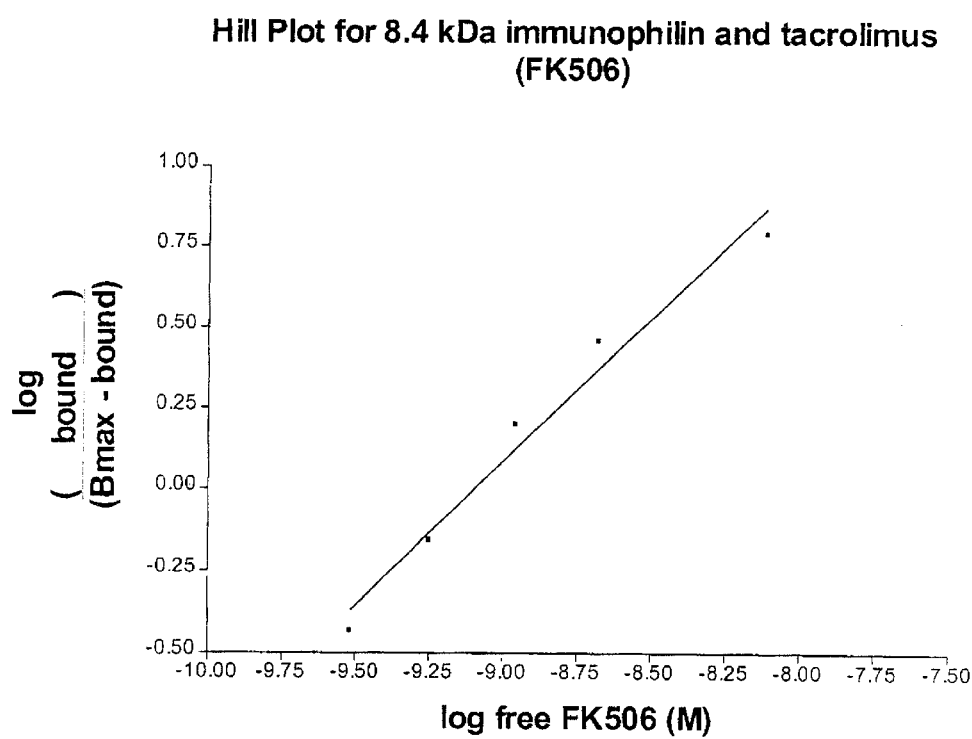
FIG. 4 shows a Hill plot for the binding of radioactive FK-506 to the 8.4 kDa immunophilin.

Example 4
Binding Constants of Ubiquitin and the Isolated 8.4 kDa Immunophilins Calf thymus 8.4 kDa immunophilin was subjected to saturation analyses with tritiated FK-506. Using Version 3.0 of the Equilibrium Binding Data Analysis EBDA/LIGAND computer soltware (G. A. MacPherson, Elsevier-BIOSOFT, Cambridge, UK), a Kd of 0.8 nM was obtained. The Scatchard plot shown in FIG. 3 was linear, with a correlation coefficient of −0.984 and a Bmax of 1.66 nM/mg protein. The linear response of the Hill plot shown in FIG. 4 (correlation coefficient 0.986 and a Hill coefficient near unity (0.88) suggest that only a single class of binding sites is present.

Figure 5:
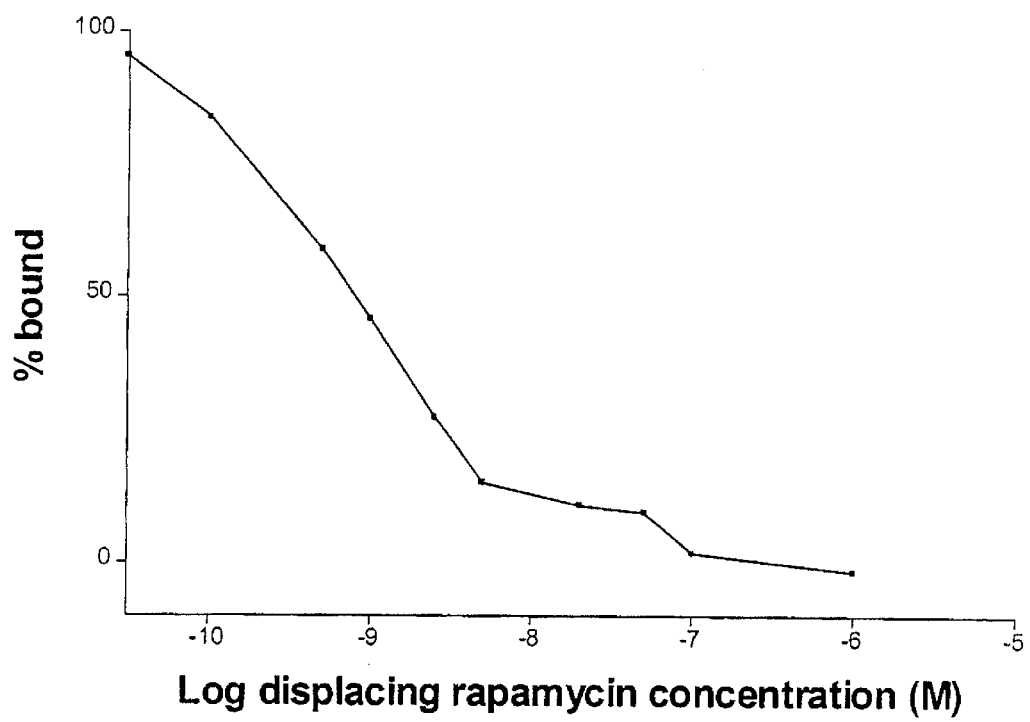
FIG. 5 shows a displacement curve of radioactive FK-506 by RAP on the 8.4 kDa immunophilin.

FIG. 5 shows the displacement of tritiated FK-506 from the 8.4 kDa immunophilin by RAP. The calculated Kd is 0.08 nM.

Figure 6:
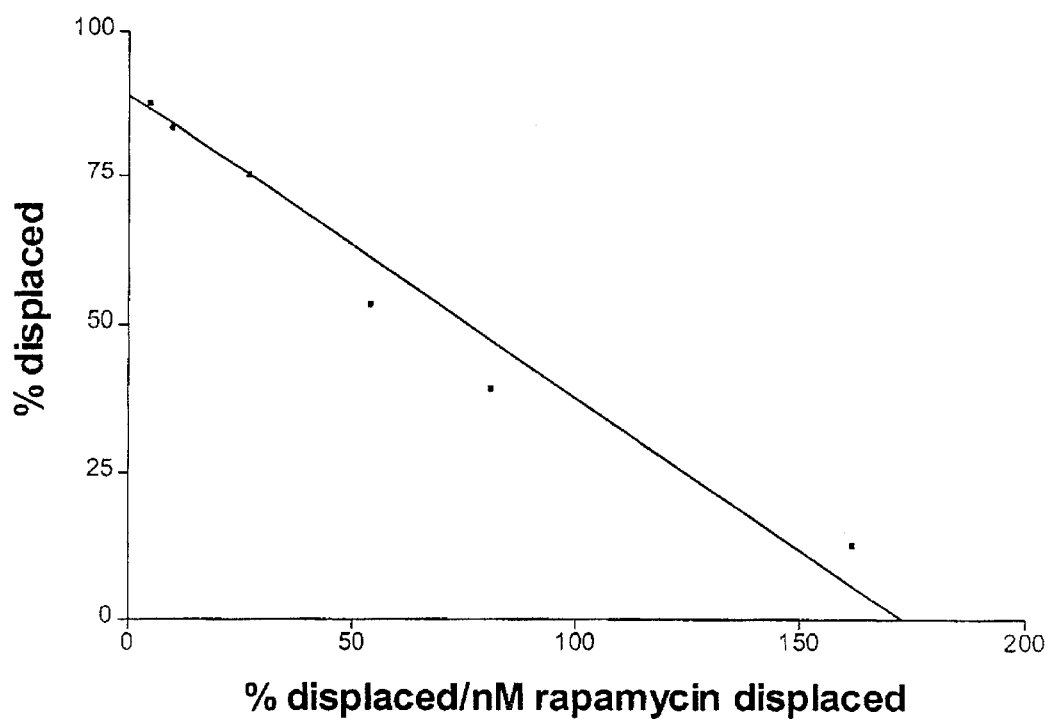
FIG. 6 shows a Hofstee plot of the data from FIG. 5.

FIG. 6 shows a linear Hofstee plot (correlation coefficient of −0.979) from the aforementioned RAP displacement experiment, indicating that there probably is only one class of binding sites for RAP on this immunophilin.

A dissociation constant for [mebmt-beta-3H]-CsA with the 8.4 kDa immunophilin could not be determined, as the binding of this drug to the protein was too low to measure (0.13%).

Example 6
Additional Biochemical Characterizations

Additional biochemical characterizations performed on the 8.4 kDa immunophilin according to previously-published methods (Davis et al. *Clin. Biochem.* 33:81 (2000) and above) showed that this protein lacks rotamase, protein kinase C, glyceraldehyde-3-P dehydrogenase and cAMP-dependent protein kinase activities, and that, when complexed to FK-506, inhibits calcineurin phosphatase.

Example 7
Analysis of Immunosuppressant Drugs in Patient Whole Blood by IBA Using Ubiquitin These assays may be performed by previously published IBA methods (see, e,g, Goodyear et al., *Clin. Biochem.* 29:457 (1996); Davis et al., *Clin. Biochem.* 33:1,31 (2000), and specification.

Example 8
Determination of Pharmacological Activity by Mixed Lymphocyte Culture (MLC) Method The MLC method for determining the pharmacological activity for immunosuppressant drugs and their metabolites and derivatives may be performed by the method of Russell et al. *Therap Drug Monitor* 13:32 (1991), as modified by Goodyear et al. 1996. Briefly, equal numbers ($10^5$ cells in 100 ul) of responder and stimulator PBMC (gamma irradiated with 3300 rads) in RPMI-1640 with L-glutamine, pen-strep, and 10% fetal bovine serum are distribuyed in 96-well plates. Polates were incubated at 37 deg. C. and 5% $CO_2$ for 6 days with either RAP or FK-506 or their metabolites or derivatives in a total volume of 250 ul. On day 6, the cultures are pulsed with 0.5 uCi [$^3$H]-thymidine for 6–8 hrs. Incorporation of the labeled thymidine was determined by harvesting the cells on glass fiber filters, and counting the radioactivity on the filters in a scintillation counter. Drug standards are suspended in 50% ethanol, and metabolites and derivatives in 100% ethanol. A standard graph is generated using parent drug concentrations ranging from 0 to 50 ug/L. Metabolites and derivatives are added at a fixed concentration of 40 ug/L. The results (DPM) may be expressed as the ratios of the metabolites and derivatives to the parent immunosuppressant drugs.

What is claimed is:

1. A protein binding assay method for the immunosuppressant drugs FK-506, rapamycin, and pharmacologically active metabolites or derivatives thereof ("analytes"), in a fluid sample, comprising the steps of:

(a) contacting said fluid sample with an isolated about 8.4 kDa binding protein ("immunophilin") so that a complex forms between said analyte and said binding protein;

(b) quantifying the amount of analyte specifically bound to said binding protein; and, (c) relating the amount of said analyte specifically bound to the concentration of said drug in said fluid sample; wherein said isolated about 8.4 kDa immunophilin exhibits the following characteristics: (i) the first 23 amino acid sequence is identical to that of authentic ubiquitin; (ii) retention times on HPLC are identical to those of authentic ubiquitin; (iii) migrates on SDS-PAGE plates identically to HPLC-purified commercial ubiquitin; (iv) exhibits a Kd of about 0.8 nM for FK-506 and 0.08 nM for rapamycin; (v) has a Hill plot value of about unity; and (vi) when complexed to FK-506 inhibits calcineurin phosphatase activity.

2. The method according to claim 1, wherein said fluid sample is derived from a human, animal or microorganism.

3. The method according to claim 1, wherein said binding protein is in free solution.

4. The method according to claim 1, wherein said binding protein is immobilized on a solid support.

5. The method according to claim 1, wherein said quantifying is by a competitive protein binding assay using a tracer amount of a labeled said immunosuppressant drug.

6. The method according to claim 5, wherein said label is a radioisotope, and said quantifying is by determination of radioactivity.

7. A method according to claim 5, wherein said label is an enzyme, said enzyme produces light from a chemiluminescent substance, and said quantifying is by determination of the amount of light produced.

8. A method according to claim 5, wherein said label is a fluorescent substance and said quantifying is by fluorescence polarization.

9. A mercantile kit for the determination of the immunosuppressive drugs FK-506, rapamycin, and pharmacologically active metabolites and derivatives thereof in a fluid sample, comprising, in separate compartments, purified isolated about 8.4 kDa immunophilin as defined in claim 1; one or more of unlabeled said immunosuppressant drugs, pharmacologically-active metabolites or derivatives thereof; and, optionally, one or more said labeled immunosuppressant drugs, pharmacologically-active metabolites or derivatives thereof.

10. A method for isolating from a fluid sample the immunosuppressant drugs FK-506, rapamycin or pharmacologically active metabolites thereof, comprising the steps of contacting said fluid sample with immobilized said isolated about 8.4 kDa immunophilin as defined in claim 1 so that a complex forms between said drug and said protein, then separating said drug from said complex.

* * * * *